US008541199B2

(12) United States Patent
Van Der Laan et al.

(10) Patent No.: US 8,541,199 B2
(45) Date of Patent: Sep. 24, 2013

(54) MUTANT PENICILLIN G ACYLASES

(75) Inventors: Jan Metske Van Der Laan, Breda (NL); Harold Monro Moody, Gulpen (NL); Richard Kerkman, Zandvoort (NL); Thomas Van Der Does, Wilnis (NL)

(73) Assignee: DSM Sinochem Pharmaceuticals Netherlands B.V., Delft (NL)

( * ) Notice: Subject to any disclaimer, the term of this patent is extended or adjusted under 35 U.S.C. 154(b) by 0 days.

(21) Appl. No.: 13/141,877

(22) PCT Filed: Dec. 22, 2009

(86) PCT No.: PCT/EP2009/067752
§ 371 (c)(1),
(2), (4) Date: Jun. 23, 2011

(87) PCT Pub. No.: WO2010/072765
PCT Pub. Date: Jul. 1, 2010

(65) Prior Publication Data
US 2011/0256585 A1 Oct. 20, 2011

(30) Foreign Application Priority Data
Dec. 23, 2008 (EP) .................................. 08172831

(51) Int. Cl.
*C12P 1/00* (2006.01)
*C12N 9/84* (2006.01)
*C12N 1/20* (2006.01)
*C07H 21/04* (2006.01)

(52) U.S. Cl.
USPC ..... 435/41; 435/230; 435/252.33; 435/320.1; 536/23.2

(58) Field of Classification Search
None
See application file for complete search history.

(56) References Cited

U.S. PATENT DOCUMENTS 6,033,823 A * 3/2000 Van Der Laan et al. ...... 430/230
6,562,958 B1 * 5/2003 Breton et al. ................. 536/23.7

FOREIGN PATENT DOCUMENTS

| WO | WO 96/05318 | 2/1996 |
| WO | WO 98/20120 | 5/1998 |
| WO | WO 03/055998 | 7/2003 |
| WO | WO 2005/003367 | 1/2005 |
| WO | WO 2006/069984 | 7/2006 |

OTHER PUBLICATIONS

Ljubijankic et al. DNA Sequence (1992) 3, 195-200.*
International Search Report for PCT/EP2009/067752, mailed Jul. 9, 2010.
Gabor et al., "Increasing the synthetic performance of penicillin acylase PAS2 by structure-inspired semi-random mutagenesis", *Protein Engineering Design & Selection*, vol. 17, No. 7, Jul. 2004, pp. 571-579.
Wang et al., "Increasing synthetic performance of penicillin G acylase from *Bacillus megaterium* by site-directed mutagenesis", *Applied Microbiology and Biotechnology*, vol. 74, No. 5, Apr. 2007, pp. 1023-1030.
Wynand et al., "The role hydrophobic active-site residues in substrate specificity and acyl transfer activity of penicillin acylase", *European Journal of Biochemistry*, vol. 269, No. 8, Apr. 2002, pp. 2093-2100.
Wynand et al., "Structural and kinetic studies on ligand binding in wild-type and active-site mutants of penicillin acylase", *Protein Engineering Design & Selection*, vol. 17, No. 5, May 2004, pp. 473-480.
Jager et al., "Saturation mutagenesis reveals the important of residues alphaR145 and alphaF146 of penicillin acylase in the synthesis of beta-lactam antibiotics", *Journal of Biotechnology*, vol. 133, No. 1, Nov. 2007, pp. 18-26.
Chandel et al., "The realm of penicillin G acylase in beta-lactam antibiotics", *Enzyme and Microbial Technology*, vol. 42, No. 3, Jan. 2008, pp. 199-207.
Jeyaprakash et al., "Recent biotechnological interventions for developing improved penicillin G acylases", *Journal of Bioscience and Bioengineering*, vol. 97, No. 1, 2004, pp. 1-13.
Charles et al., "Improved beta-lactam acylases and their use as industrial biocatalysts", *Current Opinion in Biotechnology*, vol. 15, No. 4, Aug. 2004, pp. 349-355.
Arroyo et al., "Biotechnological applications of penicillin acylases: State-of-the-art", *Applied Microbiology and Biotechnology*, vol. 60, No. 5, Jan. 2003, pp. 507-514.
Gabor et al., "A novel penicillin acylase from the environmental gene pool with improved synthetic properties", *Enzyme and Microbial Technology*, vol. 36, No. 2-3, pp. 182-190, (2005).

* cited by examiner

*Primary Examiner* — Nashaat Nashed
(74) *Attorney, Agent, or Firm* — Nixon & Vanderhye P.C.

(57) ABSTRACT

The present invention relates to a mutant prokaryotic penicillin G acylase derived from a wild-type penicillin G acylase characterized in that the mutant is having an amino acid substitution at one or more amino acid positions selected from the group consisting of amino acid positions A3, A77, A90, A144 A192, B24, B109, B148, B313, B460 and B488 according to the amino acid numbering of the *Escherichia coli* penicillin G acylase having the amino acid sequence depicted in SEQ ID No: 1.

13 Claims, No Drawings

SEQUENCE LISTING

<160> NUMBER OF SEQ ID NOS: 1

<210> SEQ ID NO 1
<211> LENGTH: 846
<212> TYPE: PRT
<213> ORGANISM: Escherichia coli

<400> SEQUENCE: 1

```
Met Lys Asn Arg Asn Arg Met Ile Val Asn Cys Val Thr Ala Ser Leu
 1               5                  10                  15

Met Tyr Tyr Trp Ser Leu Pro Ala Leu Ala Glu Gln Ser Ser Ser Glu
            20                  25                  30

Ile Lys Ile Val Arg Asp Glu Tyr Gly Met Pro His Ile Tyr Ala Asn
        35                  40                  45

Asp Thr Trp His Leu Phe Tyr Gly Tyr Gly Tyr Val Val Ala Gln Asp
    50                  55                  60

Arg Leu Phe Gln Met Glu Met Ala Arg Arg Ser Thr Gln Gly Thr Val
65                  70                  75                  80

Ala Glu Val Leu Gly Lys Asp Phe Val Lys Phe Asp Lys Asp Ile Arg
                85                  90                  95

Arg Asn Tyr Trp Pro Asp Ala Ile Arg Ala Gln Ile Ala Ala Leu Ser
            100                 105                 110

Pro Glu Asp Met Ser Ile Leu Gln Gly Tyr Ala Asp Gly Met Asn Ala
        115                 120                 125

Trp Ile Asp Lys Val Asn Thr Asn Pro Glu Thr Leu Leu Pro Lys Gln
    130                 135                 140

Phe Asn Thr Phe Gly Phe Thr Pro Lys Arg Trp Glu Pro Phe Asp Val
145                 150                 155                 160

Ala Met Ile Phe Val Gly Thr Met Ala Asn Arg Phe Ser Asp Ser Thr
                165                 170                 175

Ser Glu Ile Asp Asn Leu Ala Leu Leu Thr Ala Leu Lys Asp Lys Tyr
            180                 185                 190
```

-continued

Gly Val Ser Gln Gly Met Ala Val Phe Asn Gln Leu Lys Trp Leu Val
            195                 200                 205

Asn Pro Ser Ala Pro Thr Thr Ile Ala Val Gln Glu Ser Asn Tyr Pro
210                 215                 220

Leu Lys Phe Asn Gln Gln Asn Ser Gln Thr Ala Ala Leu Leu Pro Arg
225                 230                 235                 240

Tyr Asp Leu Pro Ala Pro Met Leu Asp Arg Pro Ala Lys Gly Ala Asp
                245                 250                 255

Gly Ala Leu Leu Ala Leu Thr Ala Gly Lys Asn Arg Glu Thr Ile Ala
            260                 265                 270

Ala Gln Phe Ala Gln Gly Gly Ala Asn Gly Leu Ala Gly Tyr Pro Thr
            275                 280                 285

Thr Ser Asn Met Trp Val Ile Gly Lys Ser Lys Ala Gln Asp Ala Lys
290                 295                 300

Ala Ile Met Val Asn Gly Pro Gln Phe Gly Trp Tyr Ala Pro Ala Tyr
305                 310                 315                 320

Thr Tyr Gly Ile Gly Leu His Gly Ala Gly Tyr Asp Val Thr Gly Asn
                325                 330                 335

Thr Pro Phe Ala Tyr Pro Gly Leu Val Phe Gly His Asn Gly Val Ile
            340                 345                 350

Ser Trp Gly Ser Thr Ala Gly Phe Gly Asp Asp Val Asp Ile Phe Ala
            355                 360                 365

Glu Arg Leu Ser Ala Glu Lys Pro Gly Tyr Tyr Leu His Asn Gly Lys
370                 375                 380

Trp Val Lys Met Leu Ser Arg Glu Glu Thr Ile Thr Val Lys Asn Gly
385                 390                 395                 400

Gln Ala Glu Thr Phe Thr Val Trp Arg Thr Val His Gly Asn Ile Leu
                405                 410                 415

Gln Thr Asp Gln Thr Thr Gln Thr Ala Tyr Ala Lys Ser Arg Ala Trp
            420                 425                 430

Asp Gly Lys Glu Val Ala Ser Leu Leu Ala Trp Thr His Gln Met Lys
            435                 440                 445

Ala Lys Asn Trp Gln Glu Trp Thr Gln Gln Ala Ala Lys Gln Ala Leu
450                 455                 460

Thr Ile Asn Trp Tyr Tyr Ala Asp Val Asn Gly Asn Ile Gly Tyr Val
465                 470                 475                 480

His Thr Gly Ala Tyr Pro Asp Arg Gln Ser Gly His Asp Pro Arg Leu
                485                 490                 495

Pro Val Pro Gly Thr Gly Lys Trp Asp Trp Lys Gly Leu Leu Pro Phe
            500                 505                 510

Glu Met Asn Pro Lys Val Tyr Asn Pro Gln Ser Gly Tyr Ile Ala Asn
            515                 520                 525

Trp Asn Asn Ser Pro Gln Lys Asp Tyr Pro Ala Ser Asp Leu Phe Ala
530                 535                 540

Phe Leu Trp Gly Gly Ala Asp Arg Val Thr Glu Ile Asp Arg Leu Leu
545                 550                 555                 560

Glu Gln Lys Pro Arg Leu Thr Ala Asp Gln Ala Trp Asp Val Ile Arg
                565                 570                 575

Gln Thr Ser Arg Gln Asp Leu Asn Leu Arg Leu Phe Leu Pro Thr Leu
            580                 585                 590

Gln Ala Ala Thr Ser Gly Leu Thr Gln Ser Asp Pro Arg Arg Gln Leu
            595                 600                 605

Val Glu Thr Leu Thr Arg Trp Asp Gly Ile Asn Leu Leu Asn Asp Asp
610                 615                 620

-continued

```
Gly Lys Thr Trp Gln Gln Pro Gly Ser Ala Ile Leu Asn Val Trp Leu
625             630             635             640

Thr Ser Met Leu Lys Arg Thr Val Val Ala Ala Val Pro Met Pro Phe
            645             650             655

Asp Lys Trp Tyr Ser Ala Ser Gly Tyr Glu Thr Thr Gln Asp Gly Pro
            660             665             670

Thr Gly Ser Leu Asn Ile Ser Val Gly Ala Lys Ile Leu Tyr Glu Ala
        675             680             685

Val Gln Gly Asp Lys Ser Pro Ile Pro Gln Ala Val Asp Leu Phe Ala
        690             695             700

Gly Lys Pro Gln Gln Glu Val Val Leu Ala Ala Leu Glu Asp Thr Trp
705             710             715             720

Glu Thr Leu Ser Lys Arg Tyr Gly Asn Asn Val Ser Asn Trp Lys Thr
            725             730             735

Pro Ala Met Ala Leu Thr Phe Arg Ala Asn Asn Phe Phe Gly Val Pro
            740             745             750

Gln Ala Ala Ala Glu Glu Thr Arg His Gln Ala Glu Tyr Gln Asn Arg
            755             760             765

Gly Thr Glu Asn Asp Met Ile Val Phe Ser Pro Thr Thr Ser Asp Arg
    770             775             780

Pro Val Leu Ala Trp Asp Val Val Ala Pro Gly Gln Ser Gly Phe Ile
785             790             795             800

Ala Pro Asp Gly Thr Val Asp Lys His Tyr Glu Asp Gln Leu Lys Met
            805             810             815

Tyr Glu Asn Phe Gly Arg Lys Ser Leu Trp Leu Thr Lys Gln Asp Val
            820             825             830

Glu Ala His Lys Glu Ser Gln Glu Val Leu His Val Gln Arg
            835             840             845
```

MUTANT PENICILLIN G ACYLASES

This application is the U.S. national phase of International Application No. PCT/EP2009/067752 filed 22 Dec. 2009 which designated the U.S. and claims priority to EP Patent Application No. 08172831.3 filed 23 Dec. 2008, the entire contents of each of which are hereby incorporated by reference.

FIELD OF THE INVENTION

The invention relates to a mutated penicillin acylase and a process for the preparation of a β-lactam antibiotic wherein a β-lactam nucleus is acylated with the aid of an activated side chain in the presence of a mutated penicillin acylase.

BACKGROUND OF THE INVENTION

The β-lactam family of antibiotics is the most important class of antibacterial compounds in clinical application. The narrow bactericidal spectrum of naturally occurring β-lactam antibiotics, their low acid stability and increasing resistance problems have triggered the development of semi-synthetic antibiotics (SSA's) such as the semi-synthetic penicillins (SSP's) and semi-synthetic cephalosporins (SSC's). In general, chemical synthesis of semi-synthetic β-lactam antibiotics is performed under harsh conditions using reactive intermediates and organic solvents at low temperatures, causing high downstream processing costs and processes that are environmentally unfriendly. Therefore, there is an ongoing effort to replace the traditional chemical processes by enzymatic conversion, in order to obtain a more sustainable production of semi-synthetic β-lactam antibiotics.

Natural β-lactams typically consist of the β-lactam nucleus (e.g. 6-amino-penicillanic acid (6-APA), 7-amino-desacetoxy-cephalosporanic acid (7-ADCA) and others) and a so-called side chain, which is connected to the nucleus via an amide bond. Penicillin G acylase (EC 3.5.1.11) is a hydrolytic enzyme which is broadly used to remove the side chain of penicillin G (PenG), cephalosporin G (CefG) and related antibiotics to produce the corresponding deacylated nucleus 6-APA and 7-ADCA respectively together with the liberated side chain (phenylacetic acid (PAA) in the case of PenG and CefG). These deacylated β-lactam intermediates are the building blocks of SSA's such as ampicillin, amoxicillin, oxacillin, cloxacillin, dicloxacillin, flucloxacillin, cefalexin, cefadroxil, cefradine, cefaclor, cefprozil, cefatoxime and others. For recent reviews on PenG acylases see Rajendhran J, and Gunasekaran P., J Biosci. Bioeng. (2004), 97, 1-13, Arroyo M et al., Appl Microbiol Biotechnol. (2003) 60, 507-14, Sio C F and Quax W J. Curr Opin Biotechnol. (2004), 15, 349-55, Chandel, A. K. et al. Enzyme and Microbial Technology (2008), 42, pp. 199-207.

Apart from deacylating β-lactam compounds, it has been found that PenG acylase and amino ester hydrolases can also be used to synthesize β-lactam antibiotics. In this process, the PenG acylase catalyses the condensation of an activated side chain with a deacylated β-lactam intermediate (such as 6-APA, 7-ADCA, 7-ACA and others). The enzyme-catalyzed synthesis of β-lactam antibiotics can be carried out in either an equilibrium-controlled or a kinetically controlled conversion process. Under conditions of an equilibrium-controlled conversion, the level of product accumulation that can be reached is governed by the thermodynamic equilibrium of the reaction, which is unfavourable in the case of the synthesis of semi-synthetic antibiotics, in particular when the reaction is carried out in aqueous media. In a kinetically controlled conversion the enzyme catalyses the transfer of the acyl group from the activated side chain, i.e. the acyl donor, to the β-lactam nucleus, i.e. nucleophilic acceptor. For the preparation of semi-synthetic penicillins, the activated side chain may be the amide-derivative or the methylester of an aromatic carboxylic acid. In this case, the level of product accumulation is governed by the catalytic properties of the enzyme and high non-equilibrium concentrations of the acyl-transfer product can transiently be obtained. Examples of side chain used in the synthesis of SSA's are activated phenylglycine, activated hydroxyphenylglycine, activated dihydro-phenylglycine and others.

PenG acylase catalyzes the hydrolysis of amides and esters via an acyl-enzyme intermediate in which the N-terminal serine of the β-subunit is esterified to the acyl group. In the case of hydrolysis, water attacks the acyl-enzyme and drives the hydrolysis to completion. When an amino group of an added external nucleophile (e.g. 6-APA, 7-ADCA) is present, both the nucleophile and the water may attack the acyl enzyme, yielding the desired acyl-transfer product (antibiotic) and the undesired hydrolyzed acyl donor, respectively.

The ability of PenG acylase to act as an acyl transferase, i.e. to synthesize SSA's, is already exploited on an industrial scale in the enzymatic production of various semi-synthetic β-lactam antibiotics. However, in the production of SSA's, the hydrolysis reaction by water reduces the efficiency of the transfer reaction, due to the loss of activated precursor side chains. The ratio between the rate of synthesis (S) and rate of hydrolysis (H) is an important parameter for evaluating the synthetic performance of a PenG acylase. The S/H ratio equals the molar ratio of synthesized product (SSA) compared to the hydrolysis product at defined conditions during the enzymatic acylation reaction. The synthesized product is defined herein as the β-lactam antibiotic formed from the activated side chain and the β-lactam nucleus. The hydrolysis product is defined herein as the corresponding acid of the activated side chain. For an economically attractive process, it is desirable that the S/H ratio is high, while at the same time, the enzymatic activity preferably is also sufficiently high.

The S/H ratio that is observed in a conversion is dependant on the reactants, the reaction conditions and the progress of the conversion. Youshko et al. showed that the initial value of the S/H ratio is dependent both on the kinetic properties of the enzyme and the concentration of the nucleophilic acceptor (e.g. 6-APA)—see Youshko, M. I. and Svedas, V. K., Biochemistry (Moscow) (2000), 65, 1367-1375 and Youshko, M. I. et al. Biochimica et Biophysica Acta—Proteins and Proteomics (2002), 1599, 134-140. At fixed conditions and nucleophile concentration, the initial S/H ratio can be used to compare the performance of different PenG acylases and/or different PenG acylase mutants. In addition, the performance of different PenG acylases can be compared by measuring the synthesis and the hydrolysis during the conversion as function of time, which allows for calculation of the S/H ratio at different stages of the conversion. The synthetic activity (=the rate at which the product of synthesis is formed=rate of synthesis=production rate) of a PenG acylase in an acylation reaction refers to the amount of β-lactam antibiotic formed in the acylation reaction per unit time at defined conditions. Preferably, the initial activity is determined. The initial enzymatic activity can be determined by carrying out the acylation reaction and then constructing a graph of the amount of product synthesized versus the reaction time, a so-called progress curve. In general, at the start of the conversion, the rate of product formation is relatively constant and the activity can be derived directly from the slope of the progress curve. In case the synthetic activity already starts to decline at the beginning of the conversion the initial rate should be obtained by extrapolation of the progress curve and calculation of the slope at t=0. In order to compare the activity of different PenG acylases the synthetic activity should be normalised to the same amount of protein. In the same way as for the initial rate of synthesis the initial rate of hydrolysis can be determined from a graph of the amount of the activated side chain hydrolyzed versus the reaction time.

PenG acylases have been subject of several studies involving PenG acylase mutants. An extensive list of published mutations is given Rajendhran and Gunasekara (2004)—supre vide. More recently, further studies were published by Gabor, E. M. and Janssen, D. B., Protein Engineering, Design and Selection (2004), 17, 571-579; Jager, S. A. W. et al. Journal of Biotechnology (2008), 133, 18-26; Wang, J., et al. Applied Microbiology and Biotechnology (2007), 74, 1023-1030.

International Patent Application WO96/05318 to Gist-brocades teaches how the specificity of PenG acylases can be modified by mutating the substrate binding site at one or more amino acid positions. It was shown that the S/H ratio of PenG acylases can also be tuned in this way.

In addition, International Patent Applications WO98/20120 (to Bristol-Meyers Squibb), WO03/055998 (to Gist-brocades) and Chinese Patent Application CN101177688 (to Shanghai Institute for Biological Sciences) describe a process for the enzymatic preparation of a β-lactam antibiotic from a β-lactam nucleus and an activated side chain with the aid of a PenG acylase mutant. WO98/20120 discloses mutations at amino acid positions 142 and 146 in the α-subunit and at amino acid positions 24, 56 or 177 in the β-subunit of *Escherichia coli* PenG acylase. Particularly, the PenG acylase variant with a mutation at position β24 (Fβ24A), whereby phenylalanine is replaced by alanine, appears to produce a significantly higher yield in the synthesis of penicillins and cephalosporins. However, in WO03/055998 it was shown that in processes where, instead of an ester precursor, an amide precursor, is used in combination with said mutant Fβ24A, the S/H ratio is still high, but the enzymatic activity is so low that the use of this mutant is economically much less attractive. Instead, it was shown in WO03/055998 that a PenG acylase mutant wherein arginine at position 145 in the α-subunit was replaced by leucine (Rα145L), cystein (Rα145C) or lysine (Rα145K), also showed an improved S/H ratio but, in addition, had retained a higher level of synthetic activity, especially with amide precursors. Nevertheless, the synthetic activity of all these mutants was less the synthetic activity of the wild-type PenG acylase.

CN101177688 disclosed that also of mutants of the *Bacillus megaterium* PenG acylase, an improvement of the S/H ratio was accompanied by a decrease of the synthetic activity.

EP-1418230 to TUHH-Technologie GmbH, discloses *Alcaligenes faecalis* PenG acylases for which the post-translational maturation of the α-subunit is incomplete resulting in a higher hydrolytic activity for penicillin G and 6-nitro-3-phenylacetamide benzoic acid (further referred to as NIPAB). Incomplete processing of said α-subunit was invoked by amino-acid substitutions in the so-called linker region between α and β subunit. It was not described whether or not such mutations could also increase the synthetic activity.

The prior art discussed above shows that, although it is possible to increase the S/H ratio of various mutants of PenG acylase, such improvements in the S/H ratio are accompanied by a decrease of the synthetic activity compared to the wild type PenG acylase. Therefore, the disadvantage of these mutants is that long conversion times are needed or very high concentration of mutant PenG acylases in such conversion, which makes industrial applications of such mutants economically unattractive if not impossible.

It is the purpose of the present invention to provide mutant PenG acylases which have increased S/H ratio's while maintaining or more preferably increasing the synthetic activity compared to the wild type enzyme in order to be suitable for industrial processes.

DETAILED DESCRIPTION OF THE INVENTION

In a first aspect, the invention provides a mutant prokaryotic penicillin G acylase derived from a wild-type penicillin G acylase characterized in that the mutant is having an amino acid substitution at one or more amino acid positions selected from the group consisting of amino acid positions A3, A77, A90, A144, A192, B24, B109, B148, B313, B460 and B488 according to the amino acid numbering of the *Escherichia coli* penicillin G acylase having the amino acid sequence depicted in SEQ ID No: 1 and which is depicted below:

MKNRNRMIVNCVTASLMYYWSLPALAEQSSSEIKIVRDEYGMPHIYAN

DTWHLFYGYGYVVAQDRLFQMEMARRSTQGTVAEVLGKDFVKFDKDIR

RNTWPDAIRAQIAALSPEDMSILQGYADGMNAWIDKVNTNPETLLPKQ

FNTFGFTPKRWEPFDVAMIFVGTMANFRSDSTSEIDNLALLTALKDKY

GVSQGMAVFNQLKWLVNPSAPTTIAVQESNYPLKFNQQNSQTAALLPR

YDLPAPMLDRPAKGADGALLALTAGKNRETIAAQFAQGGANGLAGYPT

TSNMWVIGKSKAQDAKAIMVNGPQFGWYAPAYTYGIGLHGAGYDVTGN

TPFAYPGLVFGHNGVISWGSTAGFGDDVDIFAERLSAEKPGYYLHNGK

WVKMLSREETITVKNGQAETFTVWRTVHGNILQTDQTTQTAYAKSRAW

DGKEVASLLAWTHQMKAKNWQEWTQQAAKQALTINWYYADVNGNIGYV

HTGAYPDRQSGHDPRLPVPGTGKWDWKGLLPFEMNPKVYNPQSGYIAN

WNNSPQKDYPASDLFAFLWGGADRVTEIDRLLRQKPRLTADQAWDVIR

QTSRQDLNLRLFLPTLQAATSGLTQSDPRRQLVETLTRWDGINLLNDD

GKTWQQPGSAILNVWLTSMLKRTVVAAVPMPFDKWYSASGYETTQDGP

TGSLNISVGAKILYEAVQGDKSPIPQAVDLFAGKPQQEVVLAALEDTW

ETLSKRYGNNVSNWKTPAMALTFRANNFFGVPQAAAEETRHQAEYQNR

GTENDMIVFSPTTSDRPVLAWDVVAPGQSGFIAPDGTVDKHYEDQLKM

YENFGRKSLWLTKQDVEAHKESQEVLHVQR

The complete polypeptide chain encoded by the gene consists of a signal peptide (26 amino acids—single underlined part), the α-subunit (209 amino acids), the connecting peptide (54 amino acids—double underlined part) and the β-subunit (557 amino acids). Both the signal peptide as well as the connecting peptide are removed during post-translational maturation thus yielding an enzymatically active penicillin G acylase composed of the α- and β-subunit. In the α-subunit the amino acids are numbered A1-A209, in the β-subunit from B1 to B557.

A wild type penicillin G acylase is defined herein as a naturally occurring penicillin G acylase. The wild-type penicillin G acylase may be any suitable wild-type penicillin G acylase and preferably is selected from the group consisting of the *Escherichia coli* penicillin G acylase having the amino acid sequence depicted in SEQ ID No: 1 and penicillin G acylases which at least 30% homologous to SEQ ID No: 1.

Preferably, the wild type penicillin G acylase is selected from the group consisting of the 19 penicillin G acylase summarized in Table 1 and which share a homology of 30% or more with the *Escherichia coli* penicillin G acylase.

TABLE 1

| Group | # | Source of the wild type penicillin G acylase | Longest Identity (%) | UNIPROT:ID* |
|---|---|---|---|---|
| I | 1 | Escherichia_coli | 100 | PAC_ECOLX |
| I | 2 | Kluyvera_cryocrescens | 86 | PAC_KLUCI |
| II | 3 | Providencia_stuartii_ATCC_2582 | 64 | B2PV17_PROST |
| II | 4 | Providencia_rettgeri | 62 | Q7WZI9_PRORE |
| II | 5 | Achromobacter_sp._CCM_4824 | 54 | Q3ZEF0_9BURK |
| II | 6 | uncultured_gamma_proteobacteri | 53 | Q6PWR5_9GAMM |
| II | 7 | Achromobacter_xylosoxidans | 53 | Q83YY8_ALCXX |
| III | 8 | Paracoccus_denitrificans_PD122 | 45 | A1BBI0_PARDP |
| III | 9 | Serratia_proteamaculans_568 | 45 | A8GGK2_SERP5 |
| III | 10 | Alcaligenes_faecalis | 43 | B5TYU3_ALCFA |
| III | 11 | Alcaligenes_faecalis | 43 | Q8VQG6_ALCFA |
| III | 12 | Alcaligenes_faecalis | 42 | B1AEQ1_ALCFA |
| III | 13 | Alcaligenes_faecalis | 42 | O34142_ALCFA |
| III | 14 | Sphingomonas_wittichii_RW1 | 41 | A5V4S1_SPHWW |
| IV | 15 | Acinetobacter_baumannii_AYE | 39 | B0V5B7_ACIBY |
| IV | 16 | Acinetobacter_baumannii_ACICU | 38 | B2I261_ACIBC |
| IV | 17 | Acinetobacter_baumannii_ATCC_17978 | 38 | A3M5T4_ACIBT |
| IV | 18 | Bacillus_megaterium | 34 | PAC_BACME |
| IV | 19 | Bacillus_badius | 34 | Q45TR7_BACBA |
| IV | 20 | Arthrobacter_viscosus | 33 | PAC_ARTVI |

*Universal Protein Resource (http://www.uniprot.org/)

More preferred are penicillin G acylases which are 40%-100% homologous to SEQ ID No: 1 (e.g. the penicillin G acylases belonging to Group I-III) even more preferred are penicillin G acylases which are 50%-100% homologous to SEQ ID No: 1 (e.g. the penicillin G acylases belonging to Group I-II) and even more preferred are penicillin G acylases which are 80%-100% homologous to SEQ ID No: 1 (e.g. the penicillin G acylases belonging to Group I). Most preferred is the wild-type penicillin G acylase from *Escherichia coli* having the amino acid sequence of SEQ ID No: 1.

A preferred mutant prokaryotic penicillin G acylase is having at least an amino acid substitution at position B24 and amino acid substitutions at one or more positions selected from the group consisting of A3, A77, A90, A144, A192, B109, B148, B313, B460 and B488. Mutations at position B24 are known in the art. WO96/05318 discloses replacement of the naturally occurring Phe at B24 in the penicillin G acylase of *Alcaligenes feacalis* by the positively charged amino acid lysine or arginine. Especially the B:F24K mutant showed an improved capacity to cleave the substrate phenylacetyl-leucine thereby liberating leucine and allowing the leucine-deficient *E. coli* strain, transformed with the gene encoding the mutant penicillin G acylase of *Alcaligenes feacalis*, to grow. WO98/20120 shows all possible mutations at position B24 of the penicillin G acylase of *Escherichia coli*. In particular the replacement of the naturally occurring Phe at B24 by Ala gave a substantial improvement in the S/H ratio during the synthesis of Cefadroxil.

It has now surprisingly been found that the combination of a mutation at B24 with one or more mutations at a position selected from the group consisting of A3, A77, A90, A144, A192, B148, B109, B313, B460 and B488 may result in penicillin acylase mutants with an increased synthetic activity and, optionally a further improved S/H ratio during synthesis reactions of various semi-synthetic cephalosporins as well as semi-synthetic penicillins compared to penicillin acylase mutants with a mutation at position B24 alone. Preferred combinants (combinant is defined herein as a mutant enzyme comprising at least two mutations compared to the wild type enzyme) comprise mutations at the positions [B24+A144] or at positions [B24+B109] or at positions [B24+B460] or at positions [B24+A144+B109] or at positions [B24+B109+B460] or at positions [B24+B144+B460] or at positions [B24+B109+B144+B460]. Other preferred combinants comprise mutations at the positions [B24+B460+A3+A192] or at the positions [B24+B460+A90] or at the positions [B24+B148+B460] or at the positions [B24+B148+B460+A3+A192] or at the positions [B24+B148+B460+A90].

Another preferred mutant prokaryotic penicillin G acylase is having at least an amino acid substitution at position B460 and optionally one or more amino acid substitutions at the positions selected from the group consisting of A3, A77, A90, A144, A192, B24, B148, B109, B313 and B488. Preferred combinants of position B460 with at least position B24 have been listed above. Other preferred combinants comprise mutations at the positions [B460+A90] or at the positions [B460+B109] or at the positions [B460+A144] or at the positions [B460+A90+B109] or at the positions [B460+A90+A144] or at the positions [B460+B109+A144] or at the positions [B460+A90+B109+A144]. Other preferred combinants comprise mutations at the positions [B460+A192] or at the positions [B460+A3] or at the positions [B460+A192+A3].

A highly preferred mutant prokaryotic penicillin G acylase is the penicillin G acylase from *Escherichia coli* having the amino acid sequence according to SEQ ID No. 1 and having amino acid substitutions at positions [B24+A144] or at positions [B24+B109] or at positions [B24+B460] or at positions [B24+A144+B109] or at positions [B24+B109+B460] or at positions [B24+B144+B460] or at positions [B24+B109+B144+B460] optionally combined with one or more amino acid substitutions at the positions selected from the group consisting of A3, A77, A90, A192, B148, B313 and B488.

Another highly preferred mutant prokaryotic penicillin G acylase is the penicillin G acylase from *Kluyveromyces cryocrescens* and having amino acid substitutions at positions [B24+A144] or at positions [B24+B109] or at positions [B24+B460] or at positions [B24+A144+B109] or at positions [B24+B109+B460] or at positions [B24+B144+B460] or at positions [B24+B109+B144+B460] optionally combined with one or more amino acid substitutions at the positions selected from the group consisting of A3, A77, A90, A192, B148, B313 and B488.

Position A3 in the wild type penicillin acylases may harbor different types of amino acids. The Escherichia coli wild type enzyme has a serine. A preferred mutation in wild type penicillin acylases comprises the replacement of the naturally occurring amino acid by leucine, isoleucine, alanine or by threonine. A highly preferred mutation in the Escherichia coli penicillin G acylase comprises A:S3A or A:S3L.

Position A77 in the wild type penicillin acylases may harbor different types of amino acids, e.g. positive (R, K) and negatively (D, E) charged residues as well as polar ones (S, N, Q). The Escherichia coli wild type enzyme has an alanine. A preferred mutation in wild type penicillin acylases comprises the replacement of the naturally occurring amino acid by threonine. A highly preferred mutation in the Escherichia coli penicillin G acylase comprises A:A77T.

acid such as aspartic acid, glutamic acid, lysine or arginine. A highly preferred mutation in the Escherichia coli penicillin G acylase comprises A:V192E.

Position B24 is highly conserved among the wild type penicillin G acylases. In the E. coli penicillin G acylase and many other wild type enzymes, phenylalanine is found. The remaining wild type enzymes also have hydrophobic residues (M, V) or a polar one (Q). A preferred mutation in wild type penicillin acylases comprises the replacement of the naturally occurring amino acid by alanine or leucine. A highly preferred mutation in the Escherichia coli penicillin G acylase comprises B:F24A or B:F24L.

Position B109 shows predominantly the positively charged amino acids lysine or arginine. In the E. coli penicillin G acylase lysine is found. A preferred mutation in wild type penicillin acylases which do not harbor a lysine, comprises the replacement of the naturally occurring amino acid by

TABLE 2

Occurrence of amino acids on positions A3, A77, A90, A144, A192, B24, B109, B148, B313, B460 and B488 in 20 wild type penicillin G acylases.

| # | Source of the wild type penicillin G acylase | Identity | A3 | A77 | A90 | A144 | A192 | B24 | B109 | B148 | B313 | B460 | B488 |
|---|---|---|---|---|---|---|---|---|---|---|---|---|---|
| 1 | Escherichia_coli | 100% | S | A | M | N | V | F | K | V | S | F | F |
| 2 | Kluyvera_cryocrescens | 86% | P | S | K | N | A | F | K | V | N | F | F |
| 3 | Providencia_stuartii_ATCC_2582 | 64% | P | S | Q | N | A | F | K | V | D | F | F |
| 4 | Providencia_rettgeri | 62% | S | S | Q | N | S | F | K | L | N | F | F |
| 5 | Achromobacter_sp._CCM_4824 | 54% | D | R | R | N | A | F | K | L | D | L | F |
| 6 | uncultured_gamma_proteobacteri | 53% | A | R | R | N | E | F | K | L | D | L | F |
| 7 | Achromobacter_xylosoxidans | 53% | A | R | R | N | P | F | K | L | D | L | F |
| 8 | Paracoccus_denitrificans_PD122 | 45% | T | D | R | G | E | F | K | I | Q | L | F |
| 9 | Serratia_proteamaculans_568 | 45% | A | K | R | N | K | F | K | V | N | L | F |
| 10 | Alcaligenes_faecalis | 43% | V | S | R | N | A | F | R | V | D | T | F |
| 11 | Alcaligenes_faecalis | 43% | V | S | R | N | A | F | R | V | N | T | F |
| 12 | Alcaligenes_faecalis | 42% | V | S | R | N | A | F | R | V | N | T | F |
| 13 | Alcaligenes_faecalis | 42% | V | S | R | N | A | F | R | V | N | T | F |
| 14 | Sphingomonas_wittichii_RW1 | 41% | Q | S | R | L | G | M | K | V | H | A | F |
| 15 | Acinetobacter_baumannii_AYE | 39% | Q | N | R | N | S | Q | K | I | T | V | L |
| 16 | Acinetobacter_baumannii_ACICU | 38% | Q | N | R | N | S | Q | K | I | T | V | L |
| 17 | Acinetobacter_baumannii_ATCC_1 | 38% | H | N | R | N | S | Q | K | I | T | V | L |
| 18 | Bacillus_megaterium | 34% | N | E | K | Y | S | V | K | A | T | I | M |
| 19 | Bacillus_badius | 34% | V | E | K | Y | P | V | R | A | E | I | M |
| 20 | Arthrobacter_viscosus | 33% | N | E | R | Y | S | V | K | A | T | I | M |

Position A90 in the wild type penicillin acylases may harbor different types of amino acids, but predominantly positively charged ones (R, K). The Escherichia coli wild type enzyme has a methionine. A preferred mutation in wild type penicillin acylases which do not harbor a lysine, comprises the replacement of the naturally occurring amino acid by lysine. A highly preferred mutation in the Escherichia coli penicillin G acylase comprises A:M90K.

Position A144 in the wild type penicillin acylases shows mostly asparagine. A preferred mutation in wild type penicillin acylases comprises the replacement of the naturally occurring amino acid by threonine. In addition aromatic amino acids tyrosine or phenylalanine or tryptophan are preferred amino acids at the position corresponding to A144 in Escherichia coli penicillin G acylase. A highly preferred mutation in the Escherichia coli penicillin G acylase comprises A:N144S.

Position A192 in the wild type penicillin acylases may harbor different types of amino acids. The Escherichia coli wild type enzyme has a valine. A preferred mutation in wild type penicillin acylases comprises the replacement of the naturally occurring amino acid by a more polar amino acid such as serine or threonine, preferably even a charged amino arginine. A highly preferred mutation in the Escherichia coli penicillin G acylase comprises B:K109R.

Position B148 in the wild type penicillin acylases may harbor different types but predominantly small hydrophobic residues (V, L, I, A). In the E. coli penicillin G acylase valine is found. A preferred mutation in wild type penicillin acylases which do not harbor a leucine, comprises the replacement of the naturally occurring amino acid by leucine. A highly preferred mutation in the Escherichia coli penicillin G acylase comprises B:V148L.

Position B313 in the wild type penicillin acylases may harbor different types but predominantly polar or negatively charged residues (S, N, D, Q, H, T, E). In the E. coli penicillin G acylase serine is found. A preferred mutation in wild type penicillin acylases which do not harbor asparagine or aspartic acid, comprises the replacement of the naturally occurring amino acid by asparagine or aspartic acid. A highly preferred mutation in the Escherichia coli penicillin G acylase comprises B:S313N.

Position B460 is less conserved among the 20 wild type penicillin G acylases. Most wild type enzymes have a hydrophobic residue (F, L, A, V, I). In the E. coli penicillin G acylase phenylalanine is found. A preferred mutation in wild type penicillin acylases which do not have a naturally occurring leucine is replacement of the naturally occurring amino acid by leucine or comprises the replacement of the naturally occurring amino acid by threonine, valine or isoleucine. A highly preferred mutation in the *Escherichia coli* penicillin G acylase comprises B:F460L. In penicillin acylase which have a leucine at the position corresponding to *Escherichia coli* penicillin G acylase B:F460, the leucine might be replaced by alanine, threonine, valine or isoleucine. In particular when combined with a mutation at the position corresponding to *Escherichia coli* penicillin G acylase B:F24.

Position B488 is highly conserved among the wild type penicillin G acylases. In the *E. coli* penicillin G acylase phenylalanine is found. A preferred mutation in wild type penicillin acylases which do not harbor a leucine or methionine, comprises the replacement of the naturally occurring amino acid by leucine or methionine. A highly preferred mutation in the *Escherichia coli* penicillin G acylase comprises B:F488L.

In a second aspect, the invention provides a nucleic acid sequence encoding the mutant penicillin G acylase of the first aspect of the invention.

In a third aspect, the invention provides an expression vector comprising the nucleic acid sequence of the second aspect of the invention.

In a fourth aspect, the invention provides a host cell comprising the expression vector of the third aspect of the invention.

In a fifth aspect, the invention provides a process for producing the mutant penicillin G acylase of the first aspect of the invention.

In a sixth aspect, the invention provides a process for the production of a semi-synthetic β-lactam antibiotic comprising an enzymatic coupling of an activated side chain to a β-lactam nucleus characterized by using the mutant prokaryotic penicillin G acylase of the first aspect of the invention. Preferred semi-synthetic β-lactam antibiotics are selected from the group consisting of semi-synthetic penicillins and semi-synthetic cephalosporins. Examples of preferred semi-synthetic penicillins are amoxicillin and ampicillin. Amoxicillin may be produced by enzymatic coupling of activated HPG (e.g. as the amide or ester, preferably the methyl ester or the ethyl ester) to 6-APA, while ampicillin may be produced by enzymatic coupling of activated PG (e.g. as the amide or ester, preferably the methyl ester or the ethyl ester) to 6-APA. Examples of preferred semi-synthetic cephalosporins are cefadroxil, cefalexin and cefradine. Cefadroxil may be produced by enzymatic coupling of activated HPG (e.g. as the amide or ester, preferably the methyl ester or the ethyl ester) to 7-ADCA, while cefalexin may be produced by enzymatic coupling of activated PG (e.g. as the amide or ester, preferably the methyl ester or the ethyl ester) to 7-ADCA and cefradine may be produced by enzymatic coupling of activated DHPG (e.g. as the amide or ester, preferably the methyl ester or the ethyl ester) to 7-ADCA.

In a preferred embodiment, the process of the invention for the production of a semi-synthetic β-lactam antibiotic comprises using a mutant prokaryotic penicillin G acylase comprising a mutation at amino acid position B24 with one or more mutations at a position selected from the group consisting of A3, A77, A90, A144, A192, B148, B109, B313, B460 and B488. Preferred mutant prokaryotic penicillin G acylases comprise mutations at the positions [B24+A144] or at positions [B24+B109] or at positions [B24+B460] or at positions [B24+A144+B109] or at positions [B24+B109+B460] or at positions [B24+B144+B460] or at positions [B24+B109+B144+B460]. Other preferred combinants comprise mutations at the positions [B24+B460+A3+A192] or at the positions [B24+B460+A90] or at the positions [B24+B148+B460] or at the positions [B24+B148+B460+A3+A192] or at the positions [B24+B148+B460+A90]. In another preferred embodiment, the process of the invention for the production of a semi-synthetic β-lactam antibiotic comprises using a mutant prokaryotic penicillin G acylase comprising a mutation at amino acid position B460 and optionally one or more amino acid substitutions at the positions selected from the group consisting of A3, A77, A90, A144, A192, B24, B148, B109, B313 and B488. Preferred combinants of position B460 with at least position B24 have been listed above. Other preferred combinants comprise mutations at the positions [B460+A90] or at the positions [B460+B109] or at the positions [B460+A144] or at the positions [B460+A90+B109] or at the positions [B460+A90+A144] or at the positions [B460+B109+A144] or at the positions [B460+A90+B109+A144]. Other preferred combinants comprise mutations at the positions [B460+A192] or at the positions [B460+A3] or at the positions [B460+A192+A3]. Highly preferred embodiments comprise using a mutant prokaryotic penicillin G acylase from *Escherichia coli* having the amino acid sequence according to SEQ ID No. 1 and having amino acid substitutions at positions [B24+A144] or at positions [B24+B109] or at positions [B24+B460] or at positions [B24+A144+B109] or at positions [B24+B109+B460] or at positions [B24+B144+B460] or at positions [B24+B109+B144+B460] optionally combined with one or more amino acid substitutions at the positions selected from the group consisting of A3, A77, A90, A192, B148, B313 and B488 or a mutant prokaryotic penicillin G acylase from *Kluyveromyces cryocrescens* and having amino acid substitutions at positions [B24+A144] or at positions [B24+B109] or at positions [B24+B460] or at positions [B24+A144+B109] or at positions [B24+B109+B460] or at positions [B24+B144+B460] or at positions [B24+B109+B144+B460] optionally combined with one or more amino acid substitutions at the positions selected from the group consisting of A3, A77, A90, A192, B148, B313 and B488.

The advantage of the process of the present invention by using the mutant prokaryotic penicillin G acylase of the invention is that, as a result of the maintained or, more preferably, increased synthetic activity and the higher S/H ratios of the mutant prokaryotic penicillin G acylases compared to the wild type enzyme, the production processes for the production of a semi-synthetic β-lactam antibiotic are very efficient. The semi-synthetic β-lactam antibiotics are produced in high yields (e.g. [mole product]/[mole β-lactam nucleus added], while hydrolysis of the activated side chains is low. Another advantage is that the processes may carried out with ratios [activated side chain]/[β-lactam nucleus] which are lower than those reported in the prior art hitherto.

The invention also provides a process for the production of amoxicillin in the presence of an enzyme catalyzing the coupling of HPG with 6-APA wherein the molar ratio of the activated HPG, preferably the ester selected from the group consisting of methyl- and ethylester to 6-APA is $\leq 3.0$, more preferably $\leq 2.5$, more preferably $\leq 2.0$, more preferably $\leq 1.5$, more preferably $\leq 1.4$, more preferably $\leq 1.3$, more preferably $\leq 1.2$, more preferably $\leq 1.1$, more preferably $\leq 1.09$, more preferably $\leq 1.08$, more preferably $\leq 1.07$, more preferably $\leq 1.06$, more preferably $\leq 1.05$, more preferably $\leq 1.04$, more preferably $\leq 1.03$ and most preferably $\leq 1.02$ and the yield of amoxicillin based on 6-APA (mole/mole) and measured after the enzymatic coupling reaction is $\geq 90\%$, preferably $\geq 91\%$, preferably $\geq 92\%$, preferably $\geq 93\%$, preferably $\geq 94\%$, preferably $\geq 95\%$ preferably $\geq 96\%$ preferably $\geq 97\%$ preferably $\geq 98\%$ and more preferably $\geq 99\%$.

Preferably the enzyme in the process for the production of amoxicillin is an acylase, preferably a penicillin-G acylase, which possesses the property of producing amoxicillin from 500 mmole per liter HPGM and 530 mmole per liter 6-APA (i.e. the conversion) and at the end of the conversion, performed under the conditions as described in Test A as disclosed herein, results in less than 5 mmole per liter 6-APA. None of the naturally occurring wild type penicillin G acylases in Table 2? possesses this property. Suitable wild type penicillin G acylases may be found by screening or, more preferably, be obtained by substituting one or more amino acids.

In a preferred embodiment of the process of the invention, amoxicillin may be produced by using the mutant prokaryotic penicillin G acylase of the invention. A highly preferred mutant prokaryotic penicillin G acylase that may be used is the penicillin G acylase from *Escherichia coli* having the amino acid sequence according to SEQ ID No. 1 or the penicillin G acylase from *Kluyveromyces cryocrescens* and having amino acid substitutions at positions [B24+B109] or [B24+B460] or [B109+B460] or [B24+B109+B460[ or [B24+B148+B460], optionally combined with one or more amino acid substitutions at the positions selected from the group consisting of A3, A77, A90, A144, A192, B148, B313 and B488. Most preferred is the penicillin G acylase from *Escherichia coli* having the amino acid sequence according to SEQ ID No. 1 and having amino acid substitutions at positions [B24+B109] or [B24+B460] or [B109+B460] or [B24+B109+B460].

MATERIALS AND METHODS

Preparation of the Acylase Mutants

The production, isolation and purification of wild type and mutant penicillin G acylases may be carried out as described in WO96/05318 and WO03/055998. Alternatively, genes encoding mutant penicillin G acylases may be obtained by gene synthesis.

Production of the mutant penicillin G acylase may be obtained by cloning the genes encoding mutant penicillin G acylases into an appropriate expression vector, transforming a suitable host such as *E. coli* with said vector and culturing the transformed host under conditions suitable for the production of the mutant penicillin G acylases. Recovery and purification of the mutants was carried out as described in WO9605318. Furthermore, an Äkta Purifier 10 system, equipped with a Superdex200 gel filtration column as well as a HPLC system equipped with a TSKgel 3000SWxl column were used to purify the acylases. Both systems were running in 0.1M phosphate buffer pH7.0 at a flow rate of 1 ml/min.

Determination of the Acylase Concentration

The acylase concentration was determined by performing an active site titration with phenylmethylsulfonylfluoride (PMSF) as described by Svedas et al. 1977, Bioorg. Khimya [Russ.] 3, 546-553 and Alkema et al. 1999, Anal. Biochem 275, 47-53. Initial activities and residual activities upon active site titration were measured using NIPAB as a substrate. The hydrolysis of NIPAB is followed at 37° C. in 0.1M MOPS buffer pH=7.4 by measuring the increase in absorbance at 405 nm due to the release of 5-amino-2-nitrobenzoic acid. Alternatively, residual activities after an active site titration can be measured using the synthesis of cefalexin (see below).

Immobilization of Acylases

The various acylases were immobilized according to the method disclosed in WO97/04086 and EP0222462.

Detection of Cephalosporins

The detection of cephalosporins such as cefalexin and cefradine was carried out according to the Fujii method (Fujii et al., 1976, Process Biochemistry, 21-24). The method can easily be converted to a high throughput format screening.

Detection of Cefalexin

The standard assay to measure the formation of cefalexin from the D-phenylglycine methylester (PGM) and 7-ADCA was carried out in the following way: 10 µl of a penicillin G acylase solution was added to 130 µl of a substrate mixture consisting of 50 g/l PGM and 50 g/l 7-ADCA—see below for the preparation of this solution. Subsequently the reaction compartment was sealed to prevent evaporation. After incubation time of 2 hours at room temperature, 140 µl of 1M NaOH was added to stop the reaction and start the colour development. Thorough mixing prevents precipitates. After 2 hours incubation at room temperature in sealed compartments the absorbance at 490 nm was measured. For the blank experiment, water was added instead of enzyme. In case of determination of initial turn-over rates the enzyme concentrations were such that the final conversion was between 1 and 10%. Instead of varying the enzyme concentrations in order to control the conversion, alternatively the reaction time can be adapted to obtain the desired conversion. The absolute amount of cefalexin formed can be determined from a calibration line obtained when plotting the OD at 490 nm versus the cefalexin concentration (determined with samples containing a known amount of cefalexin).

In order to prepare the PGM/7-ADCA substrate mixture, 50 g PGM.MSA (PGM.MSA is the methane sulphonic acid (MSA) salt of PGM) and 50 g 7-ADCA were added to 900 ml 0.1M MOPS buffer pH=6.9. Under continuous stirring, re-adjust the pH to 6.9 using a 4M NaOH solution. Adjust the volume to 1 liter with buffer and adjust the pH again. For each experiment, a fresh solution should be made since PGM spontaneously degrades in water. For preparing the MOPS buffer dissolve 20.9 g MOPS (Sigma M-1254) in approx. 900 ml MilliQ water. Adjust the pH to 6.9 using the 4M NaOH solution and adjust the volume to 1 L with MilliQ water.

Detection of Cefradine

The standard assay to measure the formation of cefradine from the D-2,5-dihydrophenylglycine methylester (DH-PGM) and 7-ADCA was carried out in the following way as described above for cefalexin. Only the methane sulphonic acid salt of D-2,5-dihydrophenylglycine methylester (DH-PGM.MSA) was used instead of PGM.MSA.

Determination of the S/H Ratio

In order to determine the S/H ratio of a PenG acylase in the synthesis of β-lactam antibiotics, the conversion was measured as a function of time. Samples were taken at different time points to determine the composition of the conversion mixture. The reaction was stopped by lowering the pH to 2.7. The samples were analyzed by UPLC (Ultra Performance Liquid Chromatography) in order to determine the concentration of the formed acylated antibiotic, the antibiotic nucleus, the hydrolyzed side chain precursor and the side chain precursor.

The synthetic activity was determined from the slope of the curve obtained by plotting the amount of product versus the reaction time preferably between 0 and 10% conversion, in which area the formation of the product of the reaction is usually more or less linear in time. In case the synthetic activity rapidly declines during the reaction the initial rate can be obtained by extrapolation of the progress curve and calculation of the slope at t=0.

The hydrolysis activity was determined from the slope of the curve obtained by plotting the amount of hydrolyzed side chain precursor versus the reaction time preferably between 0 and 10% hydrolysis, in which area the formation of the hydrolyzed side chain precursor is usually more or less linear in time. The S/H ratio was calculated by dividing the slope of the synthetic activity by the slope of the hydrolytic activity.

Measurement of the S/H ratio for cefalexin was carried out in a reaction mixture containing 10 g/l PGM.MSA and 10 g/l 7-ADCA and for cefradine in a reaction mixture containing 10 g/l DHPGM.MSA and 10 g/l 7-ADCA. Penicillin G acylase was added such that after 4 hours 70-90% conversion was obtained. Samples of 20 µl were taken at various time points and diluted immediately with 800 µl 50 mM phosphoric acid pH=2.7 to stop the reaction.

The amounts of DHPGM, DHPG, PMSF, PGM and PG were detected at 210 nm and of 7-ADCA, cefalexin and Cefradine at 260 nm during UPLC chromatography, which was carried out according to the following protocol:

ACQUITY-Pump: Binary solvent manager
ACQUITY-Autosampler: Sample manager and sample organizer
ACQUITY-UV detector: PDA detector (80 hertz)
Column: UPLC BEH phenyl 1.7 µm 2.1×50 mm, (cat. no. 186002884)
Flow: 0.9 ml/min
Injection volume: 2 µl (partial loop)
Mobile phase A: 50 mM phosphate buffer (pH 6.0)
Mobile phase B: 100% acetonitril
Column temperature: 60° C.
Tray temperature: 10° C.
Wavelength: 210 and 260 nm
Runtime: 1 minute
Gradient profile:

|  | Time (min) | | | |
| --- | --- | --- | --- | --- |
|  | 0.00 | 0.60 | 0.80 | 0.85 |
| Mobile phase A (%) | 100 | 50 | 50 | 100 |
| Mobile phase B (%) | 0 | 50 | 50 | 0 |

Test A—Production of Amoxicillin from 6-APA and HPG Methyl Ester

A stainless steel reactor of 2 l, equipped with a sieve bottom with 140 µm pores and an agitator, was filled with the immobilized enzyme used to catalyse the coupling of HPGM to 6-APA. The volume was adjusted to 1000 ml by addition of water. The contents were cooled to 10° C., and the reactor contents were circulated over the sieve bottom by means of a peristaltic pump.

162.2 g 6-aminopenicillanic acid was added followed by addition of 144 g HPGM. The volume was adjusted to 1500 ml by addition of water. The mixture was agitated and circulated over the sieve. The temperature was maintained at 10° C. The pH was monitored. Initially the pH was about 6.3 and after some time increased to about 7, and subsequently decreased. At the point that pH was less than pH=6.3, the reaction is nearly complete. At that point (about 2 h after addition of HPGM) a sample was taken from the recirculation line filtered and analyzed for the residual 6-APA content by HPLC.

LIST OF ABBREVIATIONS

6-APA: 6-aminopenicillanic acid
7-ADCA: 7-aminodesacetoxycephalosporanic acid
AMPI: ampicillin
CEX: cefalexin
DHPG: D-2,5-Dihydrophenylglycine
DHPGM.MSA: D-2,5-Dihydrophenylglycine methyl ester methanesulfonic acid salt
EDTA: Ethylenediaminetetraacetic acid
HPGM: D-p-hydroxyphenylglycine methyl ester
PG: D-phenylglycine
PGA: D-phenylglycine amide
PGM: D-Phenylglycine methyl ester
PGM.HCL: D-phenylglycine methyl ester HCl salt
PGM.MSA: D-phenylglycine methyl ester methanesulfonic acid salt Nomenclature of Amino Acids

| Amino acid | 3-letter abbreviation | 1-letter abbreviation |
| --- | --- | --- |
| L-alanine | Ala | A |
| L-cysteine | Cys | C |
| L-asparaginic acid | Asp | D |
| L-glutaminic acid | Glu | E |
| L-phenylalanine | Phe | F |
| L-glycine | Gly | G. |
| L-histidine | His | H |
| L-isoleucine | Ile | I |
| L-lysine | Lys | K |
| L-leucine | Leu | L |
| L-methionine | Met | M |
| L-asparagine | Asn | N |
| L-proline | Pro | P |
| L-glutamine | Gl | Q |
| L-arginine | Arg | R |
| L-serine | Ser | S |
| L-threonine | Thr | T |
| L-tyrosine | Tyr | Y |
| L-valine | Val | V |
| L-tryptophan | Trp | W |

Homology & Identity

The terms "homology" or "percent identity" are used interchangeably herein. For the purpose of this invention, it is defined here that in order to determine the percent homology of two amino acid sequences or of two nucleic acid sequences, the sequences are aligned for optimal comparison purposes. In order to optimize the alignment between the two sequences gaps may be introduced in any of the two sequences that are compared. Such alignment can be carried out over the full length of the sequences being compared. Alternatively, the alignment may be carried out over a shorter length, for example over about 20, about 50, about 100 or more nucleic acids/based or amino acids. The identity is the percentage of identical matches between the two sequences over the reported aligned region.

A comparison of sequences and determination of percent identity between two sequences can be accomplished using a mathematical algorithm. The skilled person will be aware of the fact that several different computer programs are available to align two sequences and determine the homology between two sequences (Kruskal, J. B. (1983) An overview of sequence comparison In D. Sankoff and J. B. Kruskal, (ed.), Time warps, string edits and macromolecules: the theory and practice of sequence comparison, pp. 1-44 Addison Wesley). The percent identity between two amino acid sequences may be determined using the Needleman and Wunsch algorithm for the alignment of two sequences. (Needleman, S. B. and Wunsch, C. D. (1970) J. Mol. Biol. 48, 443-453). The algorithm can align both amino acid sequences and nucleotide sequences. The Needleman-Wunsch algorithm has been implemented in the computer program NEEDLE. For the purpose of this invention the NEEDLE program from the EMBOSS package was used (version 2.8.0 or higher, *EMBOSS: The European Molecular Biology Open Software Suite* (2000) Rice, P. Longden, I. and Bleasby, A. Trends in Genetics 16, (6) pp 276-277, URL emboss[dot]bioinformatics[dot]nl. For protein sequences, EBLOSUM62 is used for the substitution matrix. For nucleotide sequences, EDNAFULL is used. Others can be specified. The optional parameters used are a gap-open penalty of 10 and a gap extension penalty of 0.5. The skilled person will appreciate that all these different parameters will yield slightly different results but that the overall percentage identity of two sequences is not significantly altered when using different algorithms.

Global Homology Definition

The homology or identity is the percentage of identical matches between the two sequences over the total aligned region including any gaps. The homology or identity between the two aligned sequences is calculated as follows: Number of corresponding positions in the alignment showing an identical amino acid in both sequences divided by the total length of the alignment including the gaps. The identity defined as herein can be obtained from NEEDLE and is labelled in the output of the program as "IDENTITY".

Longest Identity Definition

The homology or identity between the two aligned sequences is calculated as follows: Number of corresponding positions in the alignment showing an identical amino acid in both sequences divided by the total length of the alignment after subtraction of the total number of gaps in the alignment. The identity defined as herein can be obtained from NEEDLE by using the NOBRIEF option and is labelled in the output of the program as "longest-identity".

EXAMPLES

Example 1

Selection of Penicillin G Acylase Mutants Having an Improved Cefalexin Synthesizing Activity In order to find amino acid positions and mutations which improve the activity of a PenG acylase mutant with an improved S/H ratio, a mutant library was generated by error prone mutagenesis of the gene encoding penicillin G acylase of *Escherichia coli* which contained already the following two mutations on protein level: B:F24A and B:V148L (subsequently designated as the control). The mutant library thus obtained was subjected to high throughput screening for mutants exhibiting improved cefalexin productivity compared with the control. The assay and the method of detection of the cefalexin formed by the fujii method have been described in the Materials and Methods section. For the height throughput the term productivity refers to the amount of cefalexin synthesised by a fixed amount of cell free extract (CVE) in a certain time. In total about 7000 clones were tested.

Next recombinant *Escherichia coli* cells expressing the mutants of interest and control penicillin acylases were grown as described. Shake flasks with similar $OD_{600\,nm}$ values were taken and the cultures were centrifuged and frozen at −20° C. In order to prepare a cell free extract, the pellets were resuspended in extraction buffer, 0.05M MOPS, pH=6.9 containing 0.1 mg/ml DNase and 2 mg/ml Lysozyme and incubated. After 30 minutes the extract was centrifuged and the supernatant containing the acylase activity was used for the cefalexin synthesis test. After 2 hours the conversion was stopped and the amount of cefalexin formed was determined as described in the Materials and Methods and expressed as the OD at 490 nm.

Mutants that were selected from the mutant library by screening for improved cefalexin production compared to the control are summarized in Table 3: S/H Mutants 1-4 have a higher activity.

TABLE 3

| | Gene number | | | | | | | | | | | | | |
|---|---|---|---|---|---|---|---|---|---|---|---|---|---|---|
| | 11 | 29 | 103 | 116 | 170 | 218 | 313 | 398 | 437 | 602 | 749 | 777 | abs | rel |
| | | | | | | Protein number | | | | | | | | |
| | 11 | A3 | A77 | A90 | A144 | A192 | B24 | B109 | B148 | B313 | B460 | B488 | | |
| AA wild type | Val | Ser | Ala | Met | Asn | Val | Phe | Lys | Val | Ser | Phe | Phe | | |
| AA Control | | | | | | | Ala | | Leu | | | | 2.1 | 1.0 |
| mutant 1 | Ala | Leu | | | | Glu | Ala | | Leu | | Leu | | 4.0 | 1.9 |
| mutant 2 | | | | Lys | | | Ala | | Leu | | Leu | | 3.5 | 1.6 |
| mutant 3 | | | Thr | | | | Ala | | Leu | Asn | | | 2.3 | 1.1 |
| mutant 4 | | | | | | | Ala | | Leu | | | Leu | 2.4 | 1.1 |
| Mutant 5 | | | | | | | Ala | | Leu | | Leu | | | |
| Mutant 6 | | | | | Ser | | Ala | | Leu | | Leu | | | |
| Mutant 7 | | | | | Ser | | Ala | Arg | Leu | | | | | |
| Mutant 8 | Ala | Leu | | | Ser | Glu | Ala | Arg | Leu | | Leu | | | |
| Mutant 9 | | | | | | | Ala | Arg | Leu | | Leu | | | |
| Mutant 10 | | | | | Ser | | Ala | Arg | Leu | | Leu | | | |
| Mutant 11 | Ala | Leu | | | | Glu | Ala | Arg | Leu | | Leu | | | |
| Mutant 12 | | | | | | | | | Leu | | Leu | | | |

The gene number represents the consecutive amino acid position as encoded by the cDNA sequence and includes the signal peptide (26 amino acids), the α-subunit (209 amino acids), the connecting peptide (54 amino acids) and the β-subunit (557 amino acids).
The protein number represents the amino acid position in the signal peptide, α-subunit, the connecting peptide and the β-subunit of the polypeptide sequence respectively.
The AA-wild type represents the amino acid on the respective position in the penicillin G acylase of *Escherichia coli*.
The AA-control represents the amino acid of a mutant which carries mutations B:F24A and B:V148L in the penicillin G acylase of *Escherichia coli*.
The two right columns show the cefalexin productivity for mutant 1 to mutant 4 as observed in the library screening.
Absolute productivity as well as relative productivity compared to the control is given.

Example 2

Selection of Penicillin G Acylase Mutants Having an Improved Ampicilline/6-APA in Synthesis of Ampicilline From the mutant library described above about 6000 clones were tested for the synthesis of ampicillin. After growing the *Escherichia coli* clones, cell free extracts were prepared as described before. Subsequently 20 microliters of cell free extract is transferred to 80 microliters of 0.05 M MOPS buffer pH=6.9 containing 12 mM PGM, 4 mM 6-APA and 10 mM ampicillin. PGM is prepared as the free base. All solutions are prepared fresh every day. Reactions are carried out at room temperatures and stopped with PMSF. Subsequently the samples are analyzed by UPLC chromatography.

Column: Waters Acquity UPLC BEH Phenyl, 50×2.1 mm, particle size 1.7 µm.

Solvent A: 50 mM Ammonium acetate pH=5.8
Solvent B: 60% acetonitrile+40% Milli-Q water
Weak wash: 5% acetonitrile+95% Milli-Q water
Strong wash: 95% acetonitrile+5% Milli-Q water
Gradient table:

| Time (min) | A% | B% | flow (ml/min) | curve |
|---|---|---|---|---|
| 0.00 | 100 | 0 | 1.20 | 1 |
| 0.40 | 100 | 0 | 1.20 | 6 |
| 0.50 | 66 | 34 | 1.20 | 6 |
| 0.90 | 66 | 34 | 1.20 | 6 |
| 1.00 | 0 | 100 | 1.20 | 6 |
| 1.40 | 0 | 100 | 1.20 | 6 |
| 1.50 | 100 | 0 | 1.20 | 6 |

Identification and quantification of the eluted compounds was done by mass spectrometry using a Waters Micromass ZQ 2000 LC Mass Spectrometer and by UV measurement in the range 190-400 nm using a Waters ACQUITY UPLC Photodiode Array (PDA) Detector. Calibration was done using the appropriate standards.

The clones were ranked according to the ratio ampicilline/6APA. Clones showing a higher ratio compared to the control were retested several times. Finally two clones which showed consistent improvement in the ampicilline/6-APA ratio with respect to the control were sequenced. Typical results for the two mutants are shown in table 4. The sequence of the clones are shown in table 3.

TABLE 4

Enzymatic conversion of 6-APA to ampicillin as a function of time.

| Time | ratio Ampi/6-APA | | |
|---|---|---|---|
| (min) | Control | Mutant 1 | Mutant 7 |
| 0 | 2.60 | 2.60 | 2.60 |
| 30 | 2.62 | 4.16 | 2.81 |
| 60 | 2.72 | 5.79 | 3.22 |
| 90 | 2.77 | 6.91 | 3.42 |
| 120 | 2.78 | 7.60 | 3.55 |

Mutants 5-6 and 8-12 were obtained by combining mutations, which were identified in screening the error prone library. Results of testing these mutants will be described in the examples below.

Example 3

Cefalexin en Cefradin Synthesising Activity of Penicillin G Acylase Mutants Selected on Improved Cefalexin Productivity The activities of the selected mutants mutant 1 to mutant 4 of Example 1 (Table 3) are based on the assumption that at similar growth of the production host more or less similar penicillin G acylase expression is obtained (similar $OD_{490\ nm}$~cell densities). In order to correct for any differences in expression level of the mutants, the concentration of the penicillin acylase in the cell free extracts was determined using the PMSF titration as described in the Materials and Methods. Based upon PMSF titration the active penicillin G acylase content can be determined without further purification so that the specific activities (in units per mg acylase) can be determined more accurately. In order to determine the initial synthetic activity in the synthesis of cefalexin and cefradin, the conversion was followed by UPLC as described in the Materials and Methods. Results are shown in Table 5.

TABLE 5

Specific activities of the selected penicillin acylase mutants of Example 1 for the synthesis of cefalexin, cefradin and the hydrolysis of NIPAB (see Materials and Methods for assay conditions) expressed in Arbitrary Units per mg acylase and as IF = improvement factor; the IF of the control is 1 by definition.

| | cefalexin synthesis | | Cefradin Synthesis | | NIPAB Hydrolysis | |
|---|---|---|---|---|---|---|
| | AU/mg | IF | AU/mg | IF | AU/mg | IF |
| Control | 31903 | 1.0 | 134 | 1.0 | 1.7 | 1.0 |
| mutant 1 | 60362 | 1.9 | 559 | 3.0 | 3.6 | 2.3 |
| mutant 2 | 52869 | 1.7 | 373 | 2.5 | 3.0 | 1.9 |
| mutant 3 | 40307 | 1.3 | 223 | 1.5 | 1.9 | 1.2 |
| mutant 4 | 32235 | 1.0 | 244 | 1.6 | 1.3 | 0.8 |

Example 4

S/H Ratios of the Penicillin G Acylase Mutants Selected on Improved Cefalexin Productivity The S/H ratio of the selected mutants 1-4 was measured as described in the Materials and Methods. During the synthesis of cefalexin progress curves were recorded. The S/H ratio for the synthesis of cefalexin and the hydrolysis of PGM was determined from these progress curves. For the same mutants progress curves were recorded during the synthesis of cefradine. The S/H ratio for the synthesis of cefradine and the hydrolysis of dihydrophenylglycine methylester was determined. Results are shown in Table 6.

TABLE 6

S/H ratio of the selected penicillin acylase mutants 1-4 compared to the control during the synthesis of cefalexin and cefradine.

| Acylase | initial S/H ratio cefalexin synthesis | IF | initial S/H ratio cefradine synthesis | IF |
|---|---|---|---|---|
| Control | 9.4 | 1.0 | 1.5 | 1.0 |

Example 5

Modification of Position B460 is Crucial for Enhancing the Synthetic Productivity of Penicillin G Acylases Mutants 5 and 12 were designed based on mutant 1. Mutant 5 is the control with in addition the phenylalanine at position B460 replaced by a leucine. Like mutant 5, in mutant 12 the phenylalanine at position B460 has been also replaced by leucine but now in addition the alanine at position B24 was reversed to phenylalanine as is observed at this position in many wild penicillin G acylases. Genes encoding mutants 5 and 12 were obtained by gene synthesis and were transformed to and expressed in *Escherichia coli* as described before. After fermentation the *Escherichia coli* cells were treated by sonification in order to release the penicillin-G acylase from the cells. After removing cell debris by centrifugation the concentration of active protein in the supernatant was determined via PMSF titration.

Mutants 5 and 12 were applied in the synthesis of cefalexin while wild type acylase (SEQ 1), the control acylase and mutant 1 were included as controls. The results are shown below.

TABLE 7

| Acylase | IF cefalexin synthesis activity (U/Mg) | initial S/H for synthesis cefalexin |
|---|---|---|
| wild type | 1.1 | 3.8 |
| control | 1.0 | 10.3 |
| mutant 1 | 3.3 | 13.2 |
| mutant 5 | 3.1 | 12.7 |
| mutant 12 | 1.6 | 3.2 |

Mutants 1, 5 and 12 have in common that the phenylalanine at position B460 has been replaced by leucine. For all three mutants this modification increases the synthetic activity without drastic decline of the S/H ratio. In most case the S/H ratio is even improved.

Example 6

Performance of Various Combinants in the Synthesis of Cefalexin and Cefradin Mutants 1 and 7 was selected from the screening for improved ampicilline/6-APA ratio when subjecting the mutant acylase to a mixture of PGM, 6-APA and ampicilline. Mutant 1 was also selected from the screening for improved productivity in the synthesis of cefalexin. The mutations observed in mutant 1 and mutant 7 can be combined in different ways. Mutants 6 and 8-11 are examples of such combinations. The mutants can be obtained by gene synthesis, transformation and expression in *Escherichia coli* as described before. Results of testing some of these mutants are shown in table 8.

TABLE 8

Performance of combinants mutant 6 and mutant 8 in the synthesis of cefalexin and cefradine compared to their parents mutant 1 and mutant 7.

| acylase | IF cefalexin synthesis activity (U/Mg) | initial S/H for synthesis cefalexin | IF cefradin synthesis activity (U/Mg) | initial S/H for synthesis cefradin |
|---|---|---|---|---|
| control | 1.0 | 9.3 | 1.0 | 1.3 |
| Mutant 1 | 3.8 | 10.1 | 5.2 | 2.0 |
| Mutant 7 | 2.6 | 9.8 | 2.9 | 1.9 |
| Mutant 6 | 3.8 | 6.9 | 6.0 | 1.8 |
| Mutant 8 | 4.2 | 6.4 | 7.0 | 2.1 |

The combinants resulting from combining mutations of mutant 1 and mutant 7 show that in certain aspects such hybrids can surpass the performance of their parents.

Example 7

Production of Amoxicillin from 6-APA and HPG Methyl Ester

A stainless steel reactor of 2 l, equipped with a sieve bottom with 140 μm pores and an agitator, was filled with the immobilized enzyme indicated in the table. The volume was adjusted to 1000 ml by addition of water. The contents were cooled to 10° C., and the reactor contents were circulated over the sieve bottom by means of a peristaltic pump.

162.2 g 6-aminopenicillanic acid was added followed by addition of HPGM (see table). The volume was adjusted to 1500 ml by addition of water. The mixture was agitated and circulated over the sieve. The temperature was maintained at 10° C. The pH was monitored. Initially the pH was about 6.3 and after some time increased to about 7, and subsequently decreased. At the point that pH was less than pH=6.3, the reaction is nearly complete. At that point (about 2 h after addition of HPGM) a sample was taken from the recirculation line filtered and analyzed by HPLC. The results of the of various experiments are presented in table 9.

The reaction mixture with mutant 1 and 1.06 equivalents of HPGM (conversion 10 in the table) is subjected to further processing. Reaction mixture is taken from below the sieve until the enzyme immob nearly blocks the sieve. Subsequently water is added to the mixture in the stainless steel reactor, and simultaneously mixture is taken from below the sieve until the total suspension collected has a volume of 3000 ml.

Conversion 10 was repeated 3 more times by adding the same amounts of 6-APA and HPGM while using the same enzyme already present in the reactor. The suspensions of these 4 consecutive conversions 10 are combined and subjected to recrystallization. The suspension is heated to 25° C., and the mixture is introduced in a series of 5 agitated vessels of 30 ml each. Mixture is transferred from one agitated vessel to the next by gravity overflow. Flow of suspension is 3000 ml/h. At the same time 35% HCl is added to the first vessel at such a rate that the precipitate in the suspension just dissolves in the series of 5 agitated vessels. The acidic solution is filtered in line over a 10 μm filter, and introduced in a crystallizer. In this crystallizer, pH is maintained at pH=3.7 by addition of 25% NaOH, temperature is maintained at 20° C. The volume is maintained at 2250 ml by gravity overflow to a second crystallizer. In this crystallizer the pH is maintained at pH=5.0 by addition of 25% NaOH at 20° C. The volume in the second crystallizer is maintained at 750 ml by gravity overflow to an agitated vessel. The contents of this vessel are cooled to 3° C. The residence time in this vessel is 4 h. The crystal suspension is filtered, washed with water (1.5 l/kg product) and dried in a ventilation stove at 35° C. until constant weight. The yield of amoxicillin trihydrate (calculated on added 6-APA) was 91% (mole/mole).

whereby the protein load of the immob-particles was the same for all acylases tested. Subsequently 21.4 g 7-ADCA and 95 g water were added at 25° C. and the pH was adjusted to 7.0 with 25% ammonia. 38 g PGM solution as obtained in Example 8 was dosed into the reactor at a constant rate in 120

TABLE 9

| Conversion | HPGM (g) | Ratio* | E. coli wild type [6-APA] (mM) | E. coli wild type [HPGM] (mM) | Control [6-APA] (mM) | Control [HPGM] (mM) | Mutant 1 [6-APA] (mM) | Mutant 1 [HPGM] (mM) |
|---|---|---|---|---|---|---|---|---|
| 1 | 184.8 | 1.36 | 14.0 | nd | | | | |
| 2 | 176.6 | 1.30 | 15.3 | 14.3 | 1.9 | 1.0 | | |
| 3 | 168.5 | 1.24 | 32.4 | 31.5 | 1.6 | 0.7 | | |
| 4 | 160.3 | 1.18 | 67.5 | 61.3 | 1.5 | 1.1 | | |
| 5 | 156.3 | 1.15 | | | 1.2 | 2.0 | | |
| 6 | 152.2 | 1.12 | | | 1.3 | 2.0 | | |
| 7 | 148.1 | 1.09 | | | 1.3 | 2.3 | | |
| 8 | 146.7 | 1.08 | | | | | 1.0 | 0.9 |
| 9 | 144.0 | 1.06 | | | 2.1 | 2.8 | 1.0 | 0.9 |
| 10 | 141.3 | 1.04 | | | | | 1.2 | 1.0 |
| 11 | 140.2 | 1.03 | | | 33.3 | 29.8 | | |
| 12 | 138.6 | 1.02 | | | | | 1.6 | 0.6 |
| 13 | 135.9 | 1.00 | | | 46.7 | 40.3 | 20.5 | 8.6 |

*molar equivalents of HPGM with respect to 6-APA

Example 8

Synthesis of a D-phenylglycine-methylester (PGM) Solution

The synthesis of the D-phenylglycine-methylester (PGM) solution was carried out essentially as described in WO2008/110527.

90 g PG was suspended in 170 ml methanol and 73.2 g concentrated sulfuric acid was added. The mixture was kept at reflux for 2 hours at approximately 73° C. and concentrated at reduced pressure (p=20 mm Hg, T=75-80° C.). 170 ml methanol was added and the mixture was kept again at reflux for 2 hours and concentrated at reduced pressure. Again, 170 ml methanol was added and the mixture was kept at reflux for 2 hours and concentrated at reduced pressure. Finally, 125 ml methanol was added. The solution was dosed into a second reactor, which had been pre-charged with 20 ml methanol, in 1 hour at 20° C. The pH was kept at 3.5 with ammonia. A solid was formed, which was removed by filtration. The resulting mother liquor was diluted with 25 ml water and concentrated at reduced pressure (p=20 mm Hg, T=40-45° C.). Finally 207.5 g PGM solution was obtained.

Example 9

Enzymatic Synthesis of Cefalexin

A reactor with a 175 μm sieve bottom was filled with the indicated amounts of different immobilized acylases min. The pH was maintained at 7.0 with ammonia. The temperature was kept at 25° C. After 30 min, 0.25 g solid cefalexin (seed) was added. Crystallization of cefalexin started at 45 min. From 120 to 150 min, the pH was kept at 7.0 with 25% sulfuric acid. Subsequently, the pH was decreased to 5.7 with 25% sulfuric acid.

The reactor was discharged through the bottom sieve with upwards stirring. The resulting cefalexin suspension was filtered through a glass filter. The resulting mother liquor was transferred back into the reactor. This sequence of steps was repeated five times. Subsequently, the enzyme was washed with 2×10 ml water. In this way, ≧8% of cefalexin was separated from the solid biocatalyst.

The cefalexin wet cake, mother liquor and wash water were combined, and the temperature was maintained at 2° C. The pH of the combined wet cake and mother liquors was decreased to 1.5 with concentrated sulfuric acid and the resulting solution was filtered through a 0.45 μm filter.

A crystallization reactor was filled with 20 g water and 1.0 g of cefalexin (seed). The above-mentioned acidic cefalexin solution was dosed into the crystallization reactor in 80 minutes at 30° C. The pH was kept at 5.0 with ammonia. Subsequently, the suspension was stirred at 20° C. for another 30 min. The suspension was filtered through a glass filter and the wet cake was washed with 2×15 ml water and 2×15 ml acetone.

TABLE 10

| Experiment | Acylase | Immobilized acylase (g) | cefalexin monohydrate (g) | Purity | Reaction Rate | S/H ratio end of reaction (180 min) |
|---|---|---|---|---|---|---|
| 1 | Control | 15 | 32.6 | >99.8% | n.d. | n.d. |
|  | Mutant 1 | 6 | 32.4 | >99.8% | n.d. | n.d. |
| 2 | Control | 10.25 | n.a. | n.a. | Same | 13.8 |
|  | Mutant 1 | 3.7 | n.a. | n.a. | Same | 12.9 | n.d. = not determined; n.a. = not applicable

Example 10

Production of Cefadroxil from 7-ADCA and HPG Methyl Ester

A reactor with a 175 μm sieve bottom was filled with the indicated amounts of different immobilized acylases. Subsequently 17.7 g 7-ADCA, 15.6 g HPGM, 0.02 g EDTA and 123 g water were added at 10° C. and the pH was adjusted to 7.2 with 25% ammonia. The enzymatic reaction was run at 10° C. and the pH was kept at 7.2 with formic acid.

TABLE 11

| Experiment | Acylase | Immobilized acylase (g) | Reaction Rate | S/H ratio end of reaction (180 min) |
|---|---|---|---|---|
| 1 | Control | 20.5 | Same | 25 |
|   | Mutant 1 | 8.2 | Same | 22 |

Example 11

Enzymatic Synthesis of Cefradine

A reactor with a 175 μm sieve bottom was filled with the indicated amounts of different immobilized acylases. Subsequently 14.82 g 7-ADCA and 50 g water were added at 20° C. and the pH was adjusted to 6.9 with 25% ammonia.

18.5 g DHPGM.MSA was dissolved in 20 ml water and the solution was dosed into the reactor at a constant rate in 150 min. The pH was maintained at 7.0 with ammonia. The temperature was kept at 20° C. After 30 min, 0.25 g solid cefradin (seed) was added. The pH was decreased to 5.7 with 25% sulfuric acid at 460 min. Due to inaccuracy of measurement of DHPG, the S/H could not be determined with sufficient accuracy.

TABLE 12

| Experiment | Acylase | Immobilized acylase (g) | Reaction Rate | S/H ratio end of reaction (180 min) |
|---|---|---|---|---|
| 1 | Control | 19.3 | Same | n.d. |
|   | Mutant 1 | 7.4 | Same |   |

The invention claimed is:

1. A mutant prokaryotic penicillin G acylase derived from a wild-type penicillin G acylase characterized in that the mutant comprises an amino acid substitution at least at position B460 and of at least one amino acid position selected from the group consisting of amino acid positions A3, A77, A90, A144, A192, B24, B109, B148, B313, B460 and B488 according to the amino acid numbering of the *Escherichia coli* penicillin G acylase with the amino acid sequence depicted in SEQ ID NO: 1,
   wherein the *Escherichia coli* penicillin G acylase consists of
   (a) a signal peptide (26 amino acids—amino acid position 1-26);
   (b) an α-subunit (209 amino acids—amino acid position 27-235);
   (c) a connecting peptide (54 amino acids—amino acid position 236-289); and
   (d) a β-subunit (557 amino acid position amino acid position 290-846);
   and wherein in the α-subunit the amino acids are numbered A1-A209, in the β-subunit from B1 to B557 and wherein the wild type penicillin G acylase is having an amino acid sequence which is 80-100% homologous to the amino acid sequence depicted in SEQ ID NO:1.

2. The mutant prokaryotic penicillin G acylase according to claim 1 wherein the mutant comprises an amino acid substitution at position B460 and an amino acid substitution at position B24.

3. The mutant prokaryotic penicillin G acylase according to claim 2 wherein the mutant comprises at least one further amino acid substitution at an amino acid position selected from the group consisting of A3, A77, A90, A192, B148, B313, and B488.

4. The mutant prokaryotic penicillin G acylase according to claim 2 wherein said mutant further comprises an amino acid substitution at amino acid position B148.

5. A nucleic acid sequence encoding the mutant penicillin G acylase of claim 1.

6. An expression vector comprising the nucleic acid sequence of claim 5.

7. A host cell comprising the expression vector of claim 6.

8. A process for the production of a semi-synthetic β-lactam antibiotic comprising an enzymatic coupling of an activated side chain whereby the side chain is selected from the group consisting of the amide derivative or the ester of HPG (hydroxyphenylglycine), PG (phenylglycine) and DHPG (dihydrophenylglycine) to a β-lactam nucleus characterized in the presence of the mutant prokaryotic penicillin G acylase of claim 1 and wherein the mutant prokaryotic penicillin G acylase catalyzes the enzymatic coupling.

9. A process according to claim 8 wherein the semi-synthetic β-lactam antibiotic is selected from the group consisting of semi-synthetic penicillins and semi-synthetic cephalosporins.

10. A process according to claim 9 wherein the semi-synthetic penicillin is amoxicillin or ampicillin.

11. A process according to claim 9 wherein the semi-synthetic cephalosporin is cefalexin, cefadroxil or cefradine.

12. A process for the production of amoxicillin wherein the process comprises contacting HPG (hydroxyphenylglycine) in activated form and 6-APA (6-amino-penicillanic acid) in the presence of the mutant prokaryotic penicillin G acylase of claim 1 and wherein the acylase catalyzes the coupling of HPG to 6-APA and wherein the molar ratio of the activated HPG to 6-APA is ≦3.0 and the yield of amoxicillin based on 6-APA (mole/mole) and measured after the enzymatic coupling reaction is ≧90%.

13. A process according to claim 12, wherein the acylase possesses the property of producing amoxicillin from 500 mmole per liter HPGM (hydroxyphenylglycine-methylester) and 530 mmole per liter 6-APA (6-amino-penicillanic acid) and at the end of the conversion, performed under the conditions as described in Test A, results in less than 5 mmole per liter 6-APA whereby the Test comprises the following steps:

filling a stainless steel reactor of 2 l, equipped with a sieve bottom with 140 μm pores and an agitator, with the immobilized mutant prokaryotic penicillin G acylase of claim 1 to catalyze the coupling of HPGM to 6-APA, adjusting the volume to 1000 ml by addition of water, cooling the contents to 10° C., circulating the reactor contents over the sieve bottom by means of a peristaltic pump, adding 162.2 g 6-aminopenicillanic acid followed by addition of 144 g HPGM, adjusting the volume to 1500 ml by addition of water, agitating the mixture and circulating over the sieve while maintaining the temperature at 10° C., monitoring the reaction by following the increase in pH from about 6.3 to about 7.0, and the subsequent decrease in pH to below 6.3 at which point the reaction is complete.

\* \* \* \* \*